A United States Patent

(12) United States Patent
McCreath et al.

(10) Patent No.: US 7,211,650 B2
(45) Date of Patent: May 1, 2007

(54) PURIFICATION OF FIBRINOGEN FROM FLUIDS BY PRECIPITATION AND HYDROPHOIC CHROMATOGRAPHY

(75) Inventors: Graham McCreath, Edinburgh (GB);
Udell Michael, Edinburgh (GB)

(73) Assignee: Pharming Intellectual Property BV, Leiden (NL)

( * ) Notice: Subject to any disclaimer, the term of this patent is extended or adjusted under 35 U.S.C. 154(b) by 0 days.

(21) Appl. No.: 09/814,371

(22) Filed: Mar. 22, 2001

(65) Prior Publication Data

US 2002/0019025 A1 Feb. 14, 2002

Related U.S. Application Data

(63) Continuation of application No. PCT/GB99/03193, filed on Sep. 24, 1999.

(60) Provisional application No. 60/103,321, filed on Oct. 7, 1998, provisional application No. 60/103,319, filed on Oct. 7, 1998.

(30) Foreign Application Priority Data

| Sep. 24, 1998 | (GB) | ................................. 9820845.7 |
| Sep. 24, 1998 | (GB) | ................................. 9820847.3 |
| Sep. 24, 1998 | (GB) | ................................. 9820848.1 |

(51) Int. Cl.
*C07K 1/20* (2006.01)
*C07K 1/14* (2006.01)
*C07K 1/30* (2006.01)
*C12N 9/48* (2006.01)

(52) U.S. Cl. ..................... 530/382; 530/421; 530/415; 435/212

(58) Field of Classification Search ................ 435/212; 530/421, 415, 382
See application file for complete search history.

(56) References Cited

U.S. PATENT DOCUMENTS

| 4,295,855 | A | * | 10/1981 | Sasaki et al. .................. 436/86 |
| 5,030,215 | A | * | 7/1991 | Morse et al. ................. 604/410 |
| 5,639,940 | A | * | 6/1997 | Garner et al. ................... 800/7 |
| 5,834,420 | A | | 11/1998 | Laub et al. ...................... 514/2 |
| 5,935,850 | A | * | 8/1999 | Clark et al. .................. 435/325 |
| 6,037,457 | A | * | 3/2000 | Lord .......................... 530/413 |
| 6,268,487 | B1 | * | 7/2001 | Kutzko et al. ............... 530/414 |

FOREIGN PATENT DOCUMENTS

| DE | 4240119 A1 * | 6/1994 |
| WO | WO 8605190 A1 * | 9/1986 |
| WO | WO 9213495 A1 * | 8/1992 |
| WO | WO 96/02571 | 2/1996 |
| WO | WO 97/42835 | 11/1997 |
| WO | WO 99/37680 | 7/1999 |

OTHER PUBLICATIONS

Eigel et al. "Plasmin-mediated proteolysis of casein in bovine milk" Proc. Nat'l. Acad. Sci. USA (1979) 76(5): 2244-2248.*
DE 4240119 English translation of full patent document by The Ralph McElroy Translation Company, Apr. 2005, ten pages including coversheet.*
Wilkins et al. "Isolation of recombinant proteins from milk"J. Cellular Biochem. (1992) 49: 333-338.*
Blomback et al. "A new method for fractionation opf proteins" Acta Chem. Scand. (1966) 20(8): 2317-2319.*
Chemical Abstracts, vol. 117, No. 5, Aug. 3, 1992, Columbus, Ohio, US; abstract No. 43773, E. Krause & M Bienert: "Separation of peptides by liquid chromatography on polyalkylene columns", J. Liq. Chrom., vol. 15, No. 10, 1992, pp. 1773-1784, abstract.
Chemical Abstracts, vol. 93, No. 5, Aug. 4, 1980 Columbus, Ohio, US; abstract No. 40663, T Vukovich et al.: "Separation of human blood clotting factors from fibrinogen and other plasma proteins by chromatography on butyl-sepahrose", Folia Haematol. (Leipzig), vol. 107, No. 1, 1980, pp. 148-151, abstract.
Chemical Abstracts, vol. 78, No. 5, Feb. 5, 1973 Columbus, Ohio, US; abstract No. 28211, B E G Blomback & M Blomback: "Precipitation of proteinaceous material", SE 347 862 A Aug. 21, 1972 abstract.
Izabella Lipinska et al., "Fibrinogen Heterogeneity In Human Plasma. Electrophoretic Demonstration And Characterization Of Two Major Fibroinogen Components", *Journal of Laboratory & Clinical Chemistry*, 84(4): 509-516 (1974).
Jacek Hawiger, "Adhesive Ends Of Fibrinogen And Its Antiadhesive Peptides: The End Of A Saga?" *Seminars in Haematology*, 32 (2): 99-109 (1995).
Victor Marder & N Rapheal Shulman, "High Molecular Weight Derivatives Of Human Fibrinogen Produced By Plasmin", *Journal of Biological Chemistry*, 244 (8): 2120-2124 (1969).
C. Rupp et al., "Fractionation Of Plasmic Fibrinogen Digest On Lysine-Agarose, Isolation Of Two Fragments D, Fragment E And Simultaneous Removal Of Plasmin", *Thrombosis Research*, 21: 117-121 (1982).
G Markus et al., Casein, "A Powerful Enhancer Of The Rate Of Plasminogen Activation", *Fibrinolysis*, 7: 229-236 (1993).
David Sierra, "Fibrin Sealant Adhesive Systems: A Review Of Their Chemistry, Material Properties And Clinical Applications", *Journal of Biomaterials Applications*, 7: 309-352 (1993).
B. Holm et al., "Purification And Characterization Of 3 Fibrinogens With Different Molecular Weights Obtained From Normal Human Plasma", *Thrombosis Research*, 37: 165-176 (1985).

* cited by examiner

*Primary Examiner*—Leon B. Lankford, Jr.
*Assistant Examiner*—Susan Hanley
(74) *Attorney, Agent, or Firm*—Drinker Biddle & Reath LLP; Daniel A. Monaco

(57) ABSTRACT

The present invention provides a method for the part purification of fibrinogen from milk, the method comprising the transfer of protease enzyme which is present in the milk, into the whey phase with the removal or partition if fibrinogen into another phase of the milk. The present invention also provides a method for obtaining fibrinogen from a fluid, the method comprising: a) contacting the fluid with a hydrophobic interaction chromatography resin under conditions where the fibrinogen binds to the resin; and b) removing the bound protein by means of elution.

7 Claims, 5 Drawing Sheets

PURIFICATION OF FIBRINOGEN FROM FLUIDS BY PRECIPITATION AND HYDROPHOIC CHROMATOGRAPHY

This is a continuation of co-pending international application PCT/GB/03193, published in English, having an international filing date of Sep. 24, 1999, which claims the benefit under 35 U.S.C. 119(e) of the filing date of provisional application Ser. No. 60/103,321, filed Oct. 7, 1998, abandoned, and the filing date of provisional application Ser. No. 60/103,319, filed Oct. 7, 1998, abandoned.

This disclosure is concerned generally with protein purification from fluids, in particular, but not exclusively from milk and specifically with the purification of human fibrinogen from the milk of transgenic non-human animals.

Fibrinogen, the main structural protein in the blood responsible for the formation of clots exists as a dimer of three polypeptide chains; the Aα (66.5 kD), Bβ (52 kD) and γ (46.5 kD) are linked through 29 disulphide bonds. The addition of asparagine-linked carbohydrates to the Bβ and γ chains results in a molecule with a molecular weight of 340 kD. Fibrinogen has a trinoda structure, a central nodule, termed the E domain. contains the amino-termini of all 6 chains including the fibrinopeptides (Fp) while the two distal nodules termed D domains contain the carboxy-termini of the Aα, Bβ and γ chains. Fibrinogen is proteolytically cleaved at the amino terminus of the Aα and Bβ chains releasing fibrinopeptides A and B (FpA & FpB) and converted to fibrin monomer by thrombin, a serine protease that is converted from its inactive form by Factor Xa. The resultant fibrin monomers non-covalently assemble into protofibrils by DE contacts on neighbouring fibrin molecules. This imposes a half staggered overlap mode of building the fibrin polymer chain. Contacts are also established lengthwise between adjacent D domains (DD contacts) leading to lateral aggregation. Another serine protease, Factor XIII is proteolytically cleaved by thrombin in the presence of $Ca^{++}$ into an activated form. This activated Factor XIII (Factor XIIIa) catalyses crosslinking of the polymerised fibrin by creating isopeptide bonds between lysine and glutamine side chains. The first glutamyl-lysyl bonds to form are on the C-terminal of the γ chains producing D—D crosslinks. Subsequently, multiple crosslinks form between adjacent Aα chains, the process of crosslinking imparts on the clot both biological stability (resistance to fibrinolysis) and mechanical stability [Sienbenlist and Mosesson Progressive Cross-Linking of Fibrin γ chains Increases Resistance to Fibrinolysis, Journal of Biological Chemistry, 269:28414–28419, 1994].

The coagulation process can readily be engineered into a self sustained adhesive system in vitro by having the fibrinogen and Factor XIII as one component and thrombin and $Ca^{++}$ as the second component which catalysis the polymerisation process. These adhesion systems, know in the art as "Fibrin Sealants" or "Fibrin Tissue Adhesives" have found numerous application in surgical procedures and as delivery devices for a range of pharmaceutically active compounds [Sierra, Fibrin Sealant Adhesive Systems: A Review of Their Chemistry, material Properties and Clinical Applications, Journal of Biomaterials Applications, 7:309–352, 1993].

It has been estimated that the annual U.S. clinical need for fibrin sealants is greatly in excess of the 300 Kg/year that can be harvested using the current cryoprecipitation methods used by plasma fractionaters. Alternative sources of fibrinogen, by far the major component in fibrin sealant, have therefore been explored with recombinant sources being favored [Butler et al., Current Progress in the Production of Recombinant Human Fibrinogen in the Milk of Transgenic animals, Thrombosis and Haemostasis, 78:537–542, 1997]. It has been shown that mammals are capable of producing transgenic human fibrinogen at levels of up to 5.0 g/L in their milk making this a commercially viable method for the production of human fibrinogen [Prunkard et al., High-level expression of recombinant human fibrinogen in the milk of transgenic mice, Nature Biotechnology, 14:867–871, 1996; Cottingham et al., Human fibrinogen from the milk of transgenic sheep. In: Tissue Sealants: Current Practice, Future Uses. Cambridge Institute, Newton Upper Falls, Mass., Mar. 30 Apr. 2, 1996 (abstract)].

Differences have been identified between recombinant human fibrinogen and fibrinogen which has been purified from human plasma. Fibrinogen which has been purified from human plasma has two alternately spliced gamima chains (γ and γ'). In contrast, recombinant human fibrinogen only has the major form γ. Further, the glycosylation of the beta and gamma chains (there is no N-linked glycosylation of the alpha chain) of recombinant human fibrinogen differs slightly from that on plasma derived fibrinogen, but is similar to the glycosylation found on other proteins expressed in the milk of transgenic animals. In addition, the Ser3 of the alpha chain of recombinant human fibrinogen is more highly phosphorylated than Ser3 of the alpha chain of plasma derived fibrinogen, although the difference in phosphorylation does not result in functional differences. Also, there are detectable differences in heterogeneity caused by C-terminal proteolysis of a number of highly protease-sensitive sites on the alpha chain. Differences of a similar magnitude are also observed between plasma-derived fibrinogen from different sources.

Milk is well known to contain a number of serine proteases; of these, the alkaline protease plasmin, which occurs in milk together with its inactive zymogen plasminogen, is the most significant protease contributing to proteolytic activity. Plasmin(ogen) concentration varies with health status of the animal e.g. mastitic animals exhibit increased proteolytic activity. Also influencing the proteolytic activity of milk is stage in lactation i.e. late lactation is associated with higher concentrations of plasmin [Politis and Ng Kwai Hang, Environmental Factors Affecting Plasmin Activity in Milk, Journal of Dairy Science, 72:1713–1718, 1989]. In milk, plasmin(ogen) is associated predominantly with the casein micelles, although it can also be found to a lesser extent in whey [Politis et al., Distribution of Plasminogen and Plasmin in Fractions of Bovine Milk, Journal of dairy Science, 75:1402–1410, 1992].

Plasmin is the serine protease that is predominantly responsible for the dissolution of fibrin clots in vivo and its presence is essential for haemostasis. It is very probable that any fibrinogen degradation product in milk is as a result of the action of milk proteases. Therefore, the presence of plasmin or other proteases in milk can be detrimental to the quality of fibrinogen that is produced by the lactating transgenic animal if steps are not taken to minimize their effect. Of equal importance is the removal of any fibrinogen degradation products that may result from the action of plasmin or other milk proteases. The use of protease inhibitors to minimize proteolysis is well established in the art and usually involves the addition of a cocktail of inhibitors of varying specificity. With transgenic animals the possibility of proteolytic damage to the recombinant protein has been realized and suggestions have been put forward to limit degradation (Wilkins and Velander, Isolation of Recombinant Proteins from Milk, Journal of Cellular Biochemistry, 49:33–338, 1992; Velander et al., PCT WO 95/22249). However, increasingly effective methods are constantly a desideratum.

In the purification of proteins from milk, one requirement is the separation of the desired protein from contaminating casein micelles. For the isolation of transgenic proteins such as AAT, the first step is precipitation with PEG or other agent, such as ammonium sulphate. This does not precipitate AAT, but precipitates casein and is therefore a good way of removing casein from the AAT. However, when this teaching was applied to transgenic fibrinogen in milk, it was found that not only did the casein precipitate, but that the fibrinogen precipitated with it. This was clearly not a suitable step for removing casein from fibrinogen. Further, the fibrinogen in the casein/fibrinogen precipitate was unstable and was very quickly proteolytically damaged, probably due to the co-precipitation with protease enzymes. The problem was thus how to separate casein from fibrinogen-like proteins in a milk sample or fraction thereof. The separation of plasmin(ogen) from casein micelles can be accomplished by incubation with agents such as 6-aminohexanoic acid ($\epsilon$-aminocaproic acid, $\epsilon$ACA). However, 6-aminohexanoic acid also increases the activation of plasminogen to plasmin which may accelerate proteolysis of any susceptible desired protein. Furthermore, the separation of plasmin (or plasminogen) from casein micelles does not assist in the separation of oasein micelles from fibrinogen-like proteins.

Accordingly, there remains a need to separate desired proteins from casein micelles without accelerating proteolysis of the desired protein.

Human plasma fibrinogen appears heterogeneous by SDS-PAGE and other methods for separating proteins based on size. A high molecular weight fraction (W Fibrinogen, Fibrinogen 1 or F1) with a molecular weight of 340,000 daltons contributes approximately 50–70% of total fibrinogen antigen. Low molecular weight fibrinogen (LMW Fibrinogen, Fibrinogen 2 or F2) with a molecular weight of approximately 300,000 daltons contributes 20–40%. The residual amount, designated as low molecular weight fibrinogen (LMW' Fibrinogen, Fibrinogen 3, F3 or Fragment X) has a molecular weight of approximately 280,000 daltons. It has been shown that the major differences in these fibrinogen molecules results from proteolytic damage to the carboxy terminus region of the A$\alpha$ chains (A$\alpha$ C-terminal region) resulting in differing lengths of A$\alpha$ chain C-terminus. Fibrinogen, purified from cryoprecipitate by the use of precipitation techniques has been shown to have partially digested A$\alpha$ chain [Stroetmann, U.S. Pat. No. 4,427,650] Although it was first thought that plasmin or plasmin-like enzymes were responsible for degradation of F1 fibrinogen to F2 and F3 sub-families [Lipinska et al., Fibrinogen Heterogeneity in Human Plasma: Electrophoretic demonstration and characterization of two major fibrinogen components, Journal of Laboratory & Clinical Chemistry, 84:509–516, 1974] it is apparent that plasmin itself is probably not responsible for the direct proteolysis of F1 to F2 fibrinogen [Dempfle et al., Fibrinogen Heterogeneity in Homozygous Plasminogen Deficiency Type 1: Further evidence that plasmin is not involved in formation of LMW and LMW'-Fibrinogen, Thrombosis and Haemostasis, 77:879–883, 1997]. It has been suggested that F2 fibrinogen may actually be a group of degradation products produced by several enzymes including matrix metalloproteases [Nakashima et al., Human Fibrinogen Heterogeneity: the COOH-terminal residues of defective A$\alpha$ chains of fibrinogen II, Blood Coagulation and Fibrinolysis, 3:361–370, 1992]. Recombinant fibrinogen expressed in CHO cells has also been shown to be heterogeneous comprising of F1 fibrinogen and a smaller F2-like sub fraction that is also lacking the C-terminal region of the A$\alpha$ chain illustrating that the recombinant fibrinogen is also susceptible to proteolysis [Gorkun et al., The conversion of fibrinogen to fibrin: Recombinant fibrinogen typifies plasma fibrinogen, Blood 89:4407–4414]. Similarly, recombinant human fibrinogen, produced in yeast, has also been shown to possess an F2-like fraction having partially degraded A$\alpha$ chains (Roy et al., Secretion of Biologically Active Fibrinogen by Yeast, Journal of Biological Chemistry, 270:23761–23767, 1995], demonstrating that Act chain damage may be expected for a range of expression hosts. As well as the major F2 and F3 fragments, there exist a range smaller fragments generated from fibrinogen termed Fibrinogen Degradation Products (FDPs). F3 is also often referred to as a FDP. These FDPs (Fragment Y, D and E) are well characterized and can be found in small amounts in human plasma.

Differences in the rate of clot formation, the structure of the final clot and the mechanical properties of the final clot have been observed by various investigators for each of the major fibrinogen fragments. Also, the presence of FDPs, and their influence on the clotting progress has been investigated. Gorkan et al., [Role of the $\alpha$C domains of fibrin in clot formation, Biochemistry 33:6986–6997, 1994] established that F1 fibrinogen is 95% clottable while F2 fibrinogen is 92% clottable. While total clottability of these two fractions appears similar, a distinct difference in clotting time i.e. onset of visible clot formation following the action of thrombin, was observed with the F2 fibrinogen exhibiting a greater lag time before clot formation. This has also been observed previously (e.g. Holm et al., 1985, Purification and Characterization of 3 Fibrinogens with different molecular weights obtained from Normal Human Plasma, Thrombosis & Haemostasis, 37:165–176) where F1 fibrinogen was observed to have a clotting time of 14 s compared to 20 s for F2 and 25 s for F3. Evidence therefore suggests that the extent of proteolysis of the A$\alpha$ c-terminus influences fibrin polymerization. The 3-dimensional structure of the clot is also influenced by the decree of degradation of the $\alpha$C regions of fibrinogen. Clots formed from F2 and F3 fibrinogen exhibit a low decree of protofibril branching with increased porosity. It has been postulated that partially degraded fibrinogens are more prone to lateral aggregation of protofibrils. This leads to the formation of thicker fibers resulting in coarser clots as observed by light scattering experiments. Further evidence for the importance of the A$\alpha$ chain C-terminus in clot formation arises from the fact that clots formed from Fibrinogen Milano III, a naturally occurring variant with truncated A$\alpha$ chains exhibits a reduced degree of protofibril branching [Furlan et al., Binding of calcium ions and their effect on clotting of Fibrinogen Milano II, a variant with truncated A$\alpha$ chains, Blood Coagulation and Fibrinolysis, 7:331–335, 1995]. Differences in mechanical properties of clots formed with different fibrinogen species has also been observed where clots formed from F2 and F3 appear less resistant to mechanical disturbances. Thromboelastogaphy (TEG) reveals that clots made from F1 fibrinogen are more elastic than clots formed from F2 fibrinogen [Hasegawa and Sasaki, Location of the binding site "b" for lateral polymerisation of fibrin, Thrombosis Research, 57:183–195, 1990]. Elasticity is a preferred property for fibrin sealants whose use may include application in joint or tendon surgery.

The C-terminal regions of the A$\alpha$ chains also serve other purposes distinct from clot formation. They enclose crosslinking sites for the transglutaminase, Factor XIIIa where FXIIIa catalyses the formation of isopeptide bond between adjacent fibrinogen molecules thereby adding strength and stability to the clot. Crosslinking also increases the clots resistance to proteolysis and is responsible for localizing other molecules involved in the clotting process to the surface of the clot most notably α2-antiplasmin, which is covalently crosslinked into the Aαchains by Factor XIIIa further enhancing the stability of the clot to proteolytic degradation [Rudchenko et al., Comparative, Structural and Functional Features of the Human αC domain and the Isolated αC Fragment, Journal of Biological Chemistry, 271:2523–2530, 1996]. Fibronectin, Thrombospondin and von Willibrands Factor are also crosslinked into this region. The Aα C-regions are also important for enhancing the activation of plasminogen by tPA on the clot surface therefore leading to effective fibrinolysis [Matsuka et al., Factor XIIIa catalysed crosslinking of Recombinant αC Fragemnts of Human Fibrinogen, Biochemistry, 35:5810–5816, 1996]. It has also been postulated that the Aα C-terminus of fibrinogen encloses specific recognition sites for platelet receptors located in residues Aα572 through Aα574 [Hawiger, Adhesive ends of fibrinogen and its adhesive peptides: The end of a saga, Seminars in Haemotology, 32:99–109, 1995]. Platelet aggregation is essential for haemostasis and therefore it may be expected that fibrinogen molecules having degraded Aα chains would be less capable of aggregating platelets.

The importance of Aα C-terminal regions to fibrinogen properties has inspired the development of techniques whereby fibrinogen molecules having varying degrees of Aα chain proteolysis can be separated for study. Various methods have been described for the separation of the major fibrinogen sub families and FDPs. For example precipitation techniques have been used to separate F1 and F2 from purified fibrinogen [Sasaki and Kito, Simplified determination of fibrinogen sub-fractions by glycine precipitation, Thrombosis and Haemostasis 42:440–443, 1979]. Holm et al., have described a method for the separation of purified plasma fibrinogen into F1, F2 & F3 subfamilies by using a series of precipitations with ammonium sulphate. F3. fragments Y, D and E have been separated based on size using size exclusion chromatography [Morder and Raphael Shulman, High molecular weight derivatives of human fibrinogen produced by plasmin, Journal of Biological Chemistry, 244:2120–2124, 1969]. These authors also demonstrated that F3 fibrinogen and FDPs Y, D and E actually possess anticoagulant activity and are inhibitory to clot formation; a non-desirable feature of a molecule used to prepare a surgical adhesive. Most attention has been paid to the terminal degradation products D and E which have been separated using anion exchange chromatography [Kemp et al., Plasmic degradation of fibrinogen: the preparation of a low molecular weight derivative of fragment D, Thrombosis and Haemostasis, 3:553–564, 1973], cation exchange chromatography [Rutjven Vermeer et al., A novel method for the purification of rat and human fibrin(ogen) degradation products, Hoppe-Seyler's Z. Physiological Chemistry, 360:633–637] lysine-SEPHAROSE (crosslinked beaded agarose). chromatography [Rupp et al., Fractionation of plasmic fibrinogen digest on Lysine agarose. Isolation of two fragments D, fragment E and simultaneous removal of plasmin, Thrombosis Research, 27:117–121, 1982] and Zinc chelated affinity chromatography [Structural features of fibrinogen associated with binding to chelated zinc, Scully and Kakkar, Biochim et Biophys. Acta., 700: 130–133, 1982]. In none of the above methods has the simultaneous separation of fibrinogen into sub-fractions F1, F2 & F3 and FDPs Y, D & E been described using a single technique.

As introduced above, plasmin is the serine protease that is predominantly responsible for the dissolution of fibrin clots in vivo and its presence is essential for haemostasis. However, as discussed previously, while the participation of plasmin in Aα chain degradation of F1 to F2 and F3 is still under debate, it is very probable that any fibrinogen degradation product in milk will be as a result of the action of milk proteases. Therefore, the presence of plasmin or other proteases in milk can be detrimental to the quality of fibrinogen that is produced by the lactating transgenic animal if steps are not taken to minimize their effect. Of equal importance is the removal of any fibrinogen degradation products that may result from the action of plasmin or other milk proteases. The use of protease inhibitors to minimize proteolysis is well established in the art and usually involves the addition of a cocktail of inhibitors of varying specificity.

From the above discussion, it is clear that the incorporation of fibrinogen degradation products (F3 fibrinogen, fragments Y, D & E) and even F2 fibrinogen into preparations whose end-use would be either as a heamostasis or sealing agents is not desirable. Techniques which can be incorporated into a purification of fibrinogen from the milk of transgenic animals which reduce fibrinogen degradation products enabling fibrinogen with a defined Aα chain integrity to be produced for varying applications would be of considerable use.

The invention provides an efficient and effective method whereby a protein produced in the milk of transgenic animals is recovered and purified.

This patent application describes techniques whereby part-purification of fibrinogen may be carried out. Precipitation techniques are used which include chemical agents capable of disrupting the interactions between protease enzymes and casein. Using these techniques it is possible to segregate fibrinogen product from damaging protease activity in the early stages of processing and, subsequently, remove protease activity. Precipitation is carried out in such a manner that enables the collection of substantially purified (up to 85%) with very little remaining protease activity. This absence of protease enzymes renders the fibrinogen more stable during subsequent processing thus improving product yield and forgoing the necessity for expensive refrigeration equipment or toxic protease inhibitors which would have to be removed.

This patent application describes chromatographic techniques for the purification of proteins, in particular fibrinogen from milk and for the removal of fibrinogen degradation products (Fragments X, Y, D, E & C-terminal A chain fragments). Using these techniques it is possible to purify fibrinogen to up to and at least 99% pure.

Also, use of these techniques allow for prior selection of fibrinogen molecules in a product with regard to the integrity of the A chain. Thus it becomes possible to select a fibrinogen product which could compose 100% F1 fibrinogen of 80% F1 fibrinogen or any lower concentration of F1. As F1 fibrinogen has superior functional characteristics with regard to clot elasticity, rigidity and stability, the ability to predetermine and therefore select the F1 content enables a range of fibrinogen products to be produced for varying purposes. The removal of degradation products also allows for a superior fibrinogen sealant in a controlled and reproducible manner.

Accordingly, the first aspect of the present invention provides a method for the part purification of a desired protein from milk, the method comprising the transfer of protease enzyme which is present in the milk into the whey phase with the removal or partition of the desired protein into another phase of the milk.

The desired proteins according to the present invention are any of those which may be produced in milk, including naturally produced milk proteins and transgenic proteins. Preferred proteins according to the present invention are those having fibrinogen-like characteristics which result in co-precipitation with casein in the presence of PEG or ammonium sulphate. Such proteins include, but are not limited to; fibrinogen, collagen, fibronectin, Factor VIII and alpha-2-macroglobulin.

The present invention is preferably in relation to the isolation of transgenic proteins from milk, that is proteins produced as a result of transgenic manipulation of an animal. This accordingly allows for the isolation of proteins, such as fibrinogen, collagen, fibronectin, Factor VIII and alpha-2-macroglobulin from animal milk which does not normally contain such proteins. The present invention is useful for the production and isolation of individual proteins per se, or proteins which have been altered in some way to facilitate transgenic expression, such as by fusion to other proteins.

In the present text, the term "part purification" means purification to a level of from 50% free from other contaminants, preferably 60, 70, 80, 90% free from other contaminants. Preferably the recovery rates are in the range 50% to about 80%, more preferably in the range 65% to 85%.

The present invention is preferably in relation to the isolation of fibrinogen, in particular transgenic fibrinogen from milk, that is fibrinogen produced as a result of transgenic manipulation of an animal. This accordingly allows for the isolation of fibrinogen from animal milk which milk does not normally contain such proteins. The present invention is useful for the production and isolation of fibrinogen protein per se, or fibrinogen which has been altered in some way to facilitate transgenic expression, such as by fusion to other proteins.

When the desired protein is fibrinogen, the method for the part purification thereof is optionally followed by a method step comprising:
(a) contacting the part purified fibrinogen with a hydrophobic interaction chromatography resin under conditions where the fibrinogen binds to the resin; and
(b) removing the bound protein by means of elution.

Preferably the part purified fibrinogen, optionally to be further purified by the steps a) and b) described above, is in a liquid form, either as a direct result of the first part of the method, or otherwise.

As used herein, the term "fibrinogen" refers to the main structural protein responsible for the formation of clots and includes the whole glycoprotein form of fibrinogen as well as other related fibrinogen species, including truncated fibrinogen, amino acid sequence variants (muteins or polymorphic variants) of fibrinogen a fibrinogen species which comprises additional residues and any naturally occurring variants thereof The same variations described in relation to fibrinogen also apply to other fibrinogen-like proteins which can be isolated from milk according to the present invention.

As use herein, "milk" is understood to be the fluid secreted from the mammary glands in animals. Milk according to present invention includes whole milk, skimmed milk, milk fraction and colosteral milk. It also includes a milk-derived fluid where the desired protein, in particular fibrinogen, was originally produced in milk.

The present invention enables the part purification of the desired protein by transferring protease enzymes present in the milk away from the phase into which the desired protein is obtained. The protease enzyme is transferred into the whey phase (whey phase being the phase/portion/fraction of milk which contains predominantly non-casein proteins) with the removal or partition of the desired protein into another phase of the milk. The removal or partition of the desired protein may be simultaneous to the transfer of the protease enzyme in the whey phase. Alternatively, it is possible to have a two-step process, whereby the protease enzyme is transferred first to the whey under conditions which retard proteolytic damage to the desired protein, followed by the removal or partition of the desired protein. Such conditions can be constructed by using protease inhibitors or low temperature. The transfer of protease enzyme into the whey phase predominately relates to the transfer of plasmin and/or plasminogen. Other milk proteases, such as serine proteases (alkaline or acid) may also be transferred.

The desired protein is recovered from the milk by the use of precipitation techniques well known to those in the art, such as by the use of protein precipitation agents including, but not exclusively, PEG, sodium sulphate, ammonium sulphate, glycine or temperature. The precipitation is preferably carried out with generally low concentrations of the chemical precipitation agents (e.g. 5–20% w/v sodium and ammonium sulphate, 5–20% w/v glycine or β-alanine; 2–15% PEG) as this reduces co-precipitation of whey proteins.

The transfer of the protease enzyme into the whey phase of the milk is preferably by the presence of lysine or lysine analogue such as ε-aminocaproic acid or other basic amino acids, such as arginine or histidine. The concentration of lysine or a lysine analogue according to the invention depends on a number of factors such as the type of milk from which the desired protein is being purified, the amount of the desired protein present and the manner of removal or partition of the desired protein from the whey phase of the milk. Concentrations typically range from 1 mM–2M, preferably 10–200 mM.

Most preferably, the method of the first aspect of the invention is repeated at least once, and up to approximately four times. This repetition can greatly increase the purity of the desired proteins in particular in respect of contaminating micelles.

The method according to the first aspect of the invention increases the stability of the part purified desired protein toward proteolysis, especially when the desired protein is a transgenic protein.

In the optional second step of the first aspect of the invention, when the desired protein is fibrinogen, a hydrophobic interaction chromatography resin is used.

Hydrophobic Interaction Chromatography (HIC) resins are known in the art and include resins such as Butyl SEPHAROSE. (Amersham Pharmacia Biotechnology), Phenyl SEPHAROSE (low and high substitution), Octyl SEPHAROSE and Alkyl SEPHAROSE, wherein SEPHAROSE is cross-linked beaded agarose (all of Amersham Pharmacia Biotechnology; other sources of HICs include Biosepra, France: E. Merck, Germany; BioRad USA).

Conditions under which the fibrinogen is contacted with the hydrophobic interaction chromatography resin to enable fibrinogen to bind to the resin include the presence of any "structure forming" salt (solution), such as ammonium sulphate, sodium sulphate and other salts as described in: Melander and Horuath, Salt Effects on Hydrophobic Interactions in Precipitation and Chromatography: An Interpretation of the Lyotropic Series, Archives of Biochemistry and Biophysics, 183:200–215, 1977 and Srinivason and Ruckenstein, Role of Physical Forces in Hydrophobic Interaction Chromatography, Separation and Purification Methods, 9:267–370, 1980. Removal of the bound protein is by means of standard elution techniques known in the art. Such elution can be carried out by decreasing the concentration of the structure forming salt, such-as decreasing the concentration of ammonium sulphate in the eluting buffer. Elution may be by gradient elution or more preferably, by a series of steps to predetermine and thus define the fibrinogen that is eluted from the column in terms of its sub-fraction ratios and hence its Aα chain integrity.

Preferably, the optional method step of the first aspect of the invention includes a step of washing the resin, to remove unbound components, between steps (a) and (b). Washing the resin is usually carried out with a washing buffer which has the same concentration of salt in it that was used for loading. A higher concentration of salt in the washing buffer is possible, but not preferred.

When the optional second method step of the first aspect of the invention is used, it preferably achieves at least one of the following;
(a) increases the purity of the fibrinogen
(b) resolves the fibrinogen into its fractions
(c) enables isolation of higher integrity fibrinogen Aα chain.

Since the present invention takes advantage of genetic manipulation of animals in order to obtain proteins from transgenic sources ("transgenic fibrinogen"), the source of the fibrinogen can be carefully selected. Preferably, the fibrinogen is human, bovine or ovine derived (that is, corresponding essentially to human, bovine or ovine fibrinogen). For medical purposes, it is preferred to employ proteins native to the intended patient. Thus human transgenic fibrinogen is preferred. Where the fibrinogen is recombinantly encoded, so that fibrinogen from a species other than the species in which it is being expressed, the glycosylation pattern may be different from the glycosylation pattern of the naturally occurring fibrinogen. A transgenic animal closer in biological taxonomy to the source of the transgenic fibrinogen may thus be preferred.

Clearly, any animal which produces milk, and animals which can be genetically manipulated to produce transgenic fibrinogen in their milk, are preferred. In this respect, animals which lactate and produce suitable milk include sheep, cow, goat, rabbit, water buffalo, pig or horse. Transgenic animals for the production of a transgenic protein according to the present invention, do not include transgenic humans.

A second aspect of the invention provides a method for the part purification of a desired protein from milk the method comprising precipitation of the desired protein in the presence of lysine or a lysine analogue. When the desired protein is fibrinogen, the method is optionally followed by a method step comprising:
(a) contacting the part purified fibrinogen with a hydrophobic interaction chromatography resin under conditions where the fibrinogen binds to the resin; and
(b) removing the bound protein by means of elution.

A related second aspect of the invention provides for the use of lysine or a lysine analogue in the purification of a desired protein from milk (preferably transgenic protein). The use of the lysine or lysine analogue in this aspect of the invention is preferably in combination with the precipitation of the desired protein.

All description and details with respect to the first aspect of the invention, also apply to the second.

The present invention further provides a useful method whereby fibrinogen is recovered from a fluid.

A third aspect of the present invention provides a method for obtaining fibrinogen from a fluid, the method comprising:
(a) contacting the fluid with a hydrophobic interaction chromatography resin under conditions where the fibrinogen binds to the resin; and
(b) removing the bound protein by means of elution.

The fluid-containing fibrinogen may be any. In particular, it is one or more animal body-fluids such as milk, blood plasma or urine. It is, in particular a fluid-containing fibrinogen which is or has been derived from a body fluid of an animal (such as one of those described above) and/or a fluid which has been used to solvate the fibrinogen, for example following a previous method step such as part-purification by precipitation.

Any animal body fluid can be used according to the method of the present invention. Preferred body fluids include milk, blood plasma or urine. Clearly, the natural production of fibrinogen in some body fluids, such as plasma, can provide an animal body fluid from which naturally occurring fibrinogen can be isolated. However, the present invention is preferably in relation to the isolation of transgenic fibrinogen as a result of transgenic manipulation of an animal. This accordingly, allows for the isolation of fibrinogen from animal body fluids which do not naturally contain fibrinogen, such as milk and urine. The present invention is useful for the production of fibrinogen per se or fibrinogen which has been altered in some way to facilitate transgenic expression, such as by fusion to other proteins.

The term "blood plasma" includes whole blood plasma and any fraction thereof. The term "urine" also refers to whole urine, or fractions thereof, in particular concentrated urine.

Preferably the fluid is milk or a milk-derived fluid. In such situations (where the fluid is milk or milk-derived) the method according to the third aspect of the invention may be optionally preceded by a method step comprising the part purification of fibrinogen from milk, the method comprising the transfer of protease enzyme which is present in the milk, into the whey phase with the removal or partition of the fibrinogen into another phase of the milk.

The optional preceding method step at least partially purifies the fibrinogen from milk, thus allowing a better purification and/or separation of fibrinogen by virtue of the HIC method step.

Clearly, any animal which produces a body fluid which may be used according to the third aspect of the invention is contemplated. Preferably, animals which can be genetically manipulated to produce transgenic fibrinogen in their milk, are preferred. In this respect, animals which lactate and produce suitable milk include sheep, goat, cow, camel, rabbit, water buffalo, pig or horse. These animals are also useful for the production of other body fluids according to the invention. Transgenic animals for the production of a transgenic protein according to the present invention, do not include transgenic humans.

In order to achieve the maximum result from the method according to the first aspect of the invention, it may be preferable to at least partially purify the fibrinogen from the animal body-fluid. Such a purification will depend on the body fluid from which the fibrinogen is derived and the nature of potential contaminates present. The fibrinogen is preferably purified to a level of from 20 through 40% before undergoing the method according to the first aspect of the invention. Any pre-purification method can be used, for example those known in the art, e.g. precipitation of fibrinogen as described in PCT WO 95/22249. The fact that the fibrinogen may already be part purified before application of the first aspect of the invention, does not detract from the fact the fibrinogen may have been originally produced in the body fluid of an animal.

All description and details in respect of features of the first and second aspects of the invention also apply to the third. The details of the option HIC step in the first and second aspects apply to the HIC step in the third aspect.

In accordance with the third aspect of the invention, a related third aspect provides the use of HIC in one or more of the following:
(a) increasing the purity of fibrinogen
(b) resolving fibrinogen into its fractions
(c) selecting of fibrinogen with high integrity of Aα chains from fibrinogen in a fluid, preferably a body fluid from an animal.

The use of HIC in the sixth aspect of the invention is preferably in combination with a salt solution as described according to the first aspect of the invention. Relevant preferred features of aspects one and two also apply to the third. The use of the HIC in all relevant aspects of the invention includes a batch format or a column format. In batch format, the liquid may be contacted with the HIC resin in a well stirred tank. Separation of the SIC resin from the liquid may then be facilitated by sedimentation or be centrifugally assisted. In column format, which is preferred, the liquid is preferably pumped through a column into which HIC resin has already been added. Column formats are preferred as they result in greater adsorption efficiency. This column format could be regarded as either a "Packed" or "Fixed" bed format. Further, "Expanded bed" or "fluidized bed" contactors may also be applicable.

A fourth aspect of the invention provides a method for obtaining fibrinogen from a fluid, the method comprising:
(a) contacting the fluid with a hydrophobic interaction chromatography resin under conditions where the fibrinogen binds to the resin; and
(b) removing the bound protein by means of elution.

Where the fluid is milk or milk-derived (preferable), the method according to the fourth aspect of the invention is optionally preceded by a method step comprising the part purification of the fibrinogen from milk, the method comprising precipitation of the desired protein in the presence of lysine or a lysine analogue.

All description and detail of features of aspects one to three also apply to the fourth.

The milk from which the fibrinogen is to be part purified is preferably derived from animals which can be "farmed" in order to produce sufficient quantities of milk from which to obtain pharmaceutical proteins and include sheep, cow, goats, rabbit, camel, water buffalo, pig or horse. Such animals may clearly be transgenically modified animals. Preferably, although not exclusively, the transgenic protein is bovine or human derived. Human derived proteins are preferable as these, when isolated and purified for pharmaceutical use from the milk of a transgenic animal are less likely to cause an unwanted immunological reaction when administered to a human in need thereof for medicinal purposes. The present invention does not relate to transgenically modified humans.

The plasminogen activation system in milk has been a focus of interest for a number of years. It is generally accepted that milk contains the primary enzymes responsible for fibrinolysis in vivo e.g. plasminogen activator (both tissue type, tPA and urokinase type, uPA], plasminogen and plasmin. The action of proteolysis is often observed during storage of milk or milk products where casein appears to be the milk protein most susceptible to degradation. It was soon illustrated that in milk, plasminogen activators, plasminogen and plasmin were associated mainly with the casein micelles and not in the whey (or serum) phase. The mechanism by which these molecules associate with casein has not been categorically determined but it is probable that as these molecules contain Kringle domians (structured polypeptide chains with an affinity for basic amino acids) these domains probably mediate their interaction with casein. Heegaard et al., 1997 [Plasminogen Activation System in Human Milk, Journal of Paediatric Gastroenterology and Nutrition, 25:159–166] have shown that casein immobilised on Sepharose is capable of binding tPA and when casein is present, the tPA catalysed conversion of plasminogen to plasmin is accelerated. This seems to suggest that the juxtaposition of casein, plasminogen and tPA results in enhanced plasminogen activation. The mechanism of enhanced activation is not clear but may be due to plasminogen undergoing a conformational chance on binding to casein resulting in a molecule more readily activated with tPA [Markus et al., Casein, A Powerful Enhancer of the rate of Plasminogen Activation, Fibrinolysis 7:229–236].

It is therefore apparent that an agent (such as Lysine or Lysine analogue) added to milk in sufficient concentration will dissociate tPA and plasmin (ogen) from casein transferring them to the whey phase.

The consequences of this are that active plasmin and plasminogen are then present in the same phase as the transgenic protein. In terms of fibrinogen, as discussed above, the result of this is that proteolysis, especially of the Aα chain will occur. It is known in the art that εACA is relatively ineffective at inhibiting primary fibrinolysis i.e Fragment X (F3) formation from fibrinogen or fibrin and it has been postulated that initial degradation of fibrin may occur independent of noncovalent plasmin-fibrin interaction (which is mediated through kringle domains on plasminogen binding to basic amino acids in the fibrinogen Aα chain), unlike the later steps which result in the formation of fragments Y, D and E. Indeed it has been shown [Francis et al., Structural and Chromatographic Heterogeneity of Normal Plasma Fibrinogen associated with the Presence of Three γ-chain types with Distinct Molecular Weights, Biochimica et Biophysica Acta, 744:155–164] that Aα chain proteolysis in commercial fibrinogen preparations proceeds during chromatographic separation into fibrinogen sub-families even with the inclusion of 20 mM ε-Aminocaproic acid and Aprotinin (a potent protease inhibitor) at 10 Kallikrein units/ml. It is therefore apparent that addition of ε-Aminocaproic acid during the purification of human fibrinogen from milk would have no beneficial, and even negative effects.

Paradoxically we have discovered that ε-aminocaproic acid is a useful aid in preventing degradation of fibrinogen during its purification from milk if it is included during a stage which partitions the fibrinogen, such as a precipitation stage. The similarity between fibrinogen and casein in terms of susceptibility to precipitation; a technique widely used in the purification of fibrinogen from plasma and cryoprecipitate [e.g. Schwarz et al., U.S. Pat. Nos. 4,362,567; 4,377,572 & 4,414,976], and in the separation of casein from milk [Swaisgood, Developments in dairy Chemistry—1: Chemistry of Milk Protein, Applied Science Publishers, NY, 1982] leads to the co-precipitation of at least part of the casein fraction when precipitating fibrinogen from milk using precipitating agents well known to those in the art (e.g. but not exclusively Zinc, Copper, sodium and ammonium salts, amino acids (e.g. glycine, β alanine), alcohol (e.g.ethanol) and polymers (e.g. polyethylene glycol, dextran or hydroxyethyl starch. Even by adding these precipitants at relatively low concentrations (e.g 5–20% w/v sodium and ammonium sulphate, 5–20% w/v glycine or β-alanine; 2–15% PEG) sufficient to precipitate fibrinogen or a majority fraction of it also co-precipitates a fraction of the casein phase including some whey proteins. This can be reduced if the precipitation is carried out more than once. The inclusion of ε-aminocaproic acid or a similar analogue of lysine during the precipitation stage (at a concentration of 10–200 mM) results in the dissociation of kringle containing proteins from casein and fibrinogen and maintains them in the solution phase while the fibrinogen is precipitated. The method of protection of the fibrinogen is therefore one of exclusion. The precipitated fibrinogen can then be reconstituted in a suitable buffer and is not only significantly less susceptible to proteolysis but also significantly more pure. Such a technique would works equally well if temperature is used as a method of precipitation. The added advantage of this invention is that not only is the ε-aminocaproic acid preventing proteolytic damage to the fibrinogen, it does not contaminate the precipitated fibrinogen as it remains in the solution phase.

A fifth aspect of the present invention provides transgenic fibrinogen, at least partly purified, having improved stability, in particular in respect of proteolysis. All preferred features of the first to fourth aspects of the invention also apply to the fifth, even though the transgenic protein of the fifth aspect may not necessarily be required to be produced according to the method of the first to fourth aspects.

All individual method steps described in aspects one to four are considered to increase the stability of the fibrinogen to proteolysis.

A sixth aspect of the invention provides fibrinogen, fibrinogen 1 (F1), fibrinogen 2 (F2), or a combination thereof, which has high integrity of Aα chains.

The seventh aspect of the invention provides fibrinogen, fibrinogen 1 (F1), fibrinogen 2 (F2), or a combination thereof, obtainable by a method according to the first to fourth aspects of the invention.

The fibrinogen, fibrinogen 1 and fibrinogen 2 are obtainable (having high Aα chains) by virtue of the HIC step.

The fibrinogen 1 and/or fibrinogen 2, according to the sixth and seventh aspects of the invention are particularly preferred for use in fibrinogen adhesives or sealants as described hereinbefore and hereinafter.

The fifth, sixth and seventh aspects of the invention preferably produce fibrinogen which is substantially free from viral contamination. Such fibrinogen can be more easily produced from non-blood products, such as those from milk or urine.

An eighth aspect of the invention provides for purified fibrinogen obtainable according to any of aspects one to four of the invention as described above. All description and details for aspects one to seven, also apply to the eighth.

The fibrinogen according to the invention may be in any suitable or convenient state, such as in a lyophilised or soluble state.

A ninth aspect of the invention provides a fibrin adhesive or sealant containing fibrinogen according to the fifth to eighth aspects of the invention. The fibrin adhesive or sealant according to the ninth aspect of the invention are, in all respects, with the exception of the particular fibrinogen used, well known and standard in the art [Sierra, Fibrin Sealant Adhesive Systems: A Review of Their Chemistry, Material Properties and Clinical Applications, Journal of Biomaterials Applications, 7:309–352, 1993; Martinowitz and Spotnitz, Fibrin Tissue Adhesives, Thrombosis and Haemostasis, 78:661–666, 1997; Radosevich et al., Fibrin Sealant:Scientific Rationale, Production Methods, Properties and Current Clinical Use, Vox Sanguinis, 72:133–143, 1997].

As used herein, the term "fibrin adhesive" or "fibrin sealant" describes a substance containing fibrinogen which is capable of forming a biodegradable adhesive or seal by the formation of polymerised fibrin. Such adhesive/sealant systems are alternatively called "fibrin tissue adhesives" or "fibrin tissue glues". The adhesive or seal may act as, inter alia a hemostatic agent, a barrier to fluid, a space-filling matrix or a drug-delivery agent. Particular use may be found in neurosurgery, opthalmic, orthopedic or cardiothoracic surgery, skin grafting and various other types of surgery Other than fibrinogen, the fibrin adhesive or sealant may contain substances which encourage the formation of the fibrin adhesive/seal, such as thrombin, $Ca^{++}$ (e.g. $CaCl_2$) and Factor XIII (and/or Factor XIIIa[ in his text, all references to Factor XIII are also references to factor XIIIa and vice versa). While it is recognised that thrombin would be the preferred enzyme with which to incorporate into any system whereby the formation of a fibrin clot is desired, it is appreciated that there are other enzymes capable of proteolytically cleaving fibrinogen resulting in the formation of a fibrin clot. An example of this would be the snake venom enzyme Batroxobin [Weisel and Cederholm-Williams, Fibrinogen and Fibrin: Characterization, Processing and Applications, *Handbook of Biodegradable Polymers* (Series: Drug targeting and Delivery) 7:347–365, 1997]. Other components such as albumin, fibronectin, solubilisers, bulking agents and/or suitable carriers or diluents may also be included if desired.

One advantage of fibrin sealant as a biodegradable polymer is that there are natural mechanisms in the body for the efficient removal of clots and thus the fibrin sealant may be a temporary plug for hemostasis or wound healing. Various proteolytic enzymes and cells can dissolve fibrin depending on the circumstances, but the most specific mechanism involves the fibrinolytic system. The dissolution of fibrin clots under physiological conditions involves the binding of circulating plasminogen to fibrin, and the activation of plasminogen to the active protease, plasmin, by plasminogen activators which may also be, also bound to fibrin. Plasmin then cleaves fibrin at specific sites.

Depending on the situation, it may be advantageous to let the natural process of fibrin breakdown take place after applying a fibrin adhesive or sealant to a site. Indeed, this breakdown may be encouraged, for example, by the inclusion of plasminogen.

Alternatively, in some situations it may be advantageous to delay the process by including antifibrinolytic compounds which can, for example, block the conversion of plasminogen to plasmin or directly bind to the active site of plasmin to inhibit fibrinolysis. Such antifibrinolytics include $α_2$-macroglobulin, which is a primary physiological inhibitor of plasmin; aprotinin; $α_2$-antiplasmin; and ε-aminocaproic acid.

The fibrin/sealant may comprise two components, one component containing fibrinogen and Factor XIII (and/or Factor XIIIa) and the other component containing thrombin and $Ca^{++}$. Other substances as described above may be included in one or both of the components if desired.

A tenth aspect of the invention provides a kit for a fibrin adhesive or sealant comprising fibrinogen according to any one of the fourth to eighth aspects of the invention, and instructions for use or, may comprise fibrinogen according to any one of the fourth to eighth aspects of the invention in combination with (but not necessarily mixed with) one or more of: Factor XIII, Factor XIIIa, thrombin or $Ca^{++}$. Furthermore, the kit may comprise two components: fibrinogen with (but not necessarily mixed with) Factor XIII (and/or Factor XIIIa) and thrombin with (but not necessarily mixed with) $Ca^{++}$.

The components of any fibrinogen sealant, according to the present invention, including the kit forms, may be used separately, simultaneously or sequentially.

All relevant description and details in respect of the first to ninth aspects of the invention also apply to the tenth.

An eleventh aspect of the invention provides a method for producing a fibrin adhesive or sealant according to the ninth aspect of the invention, comprising admixing fibrinogen with thrombin or any other enzyme which is capable of proteolytically modifying fibrinogen and causing it to clot. Factor XIII (and/or Factor XIIIa) and $Ca^{2+}$ may also be mixed with the fibrinogen and thrombin (or other suitable enzyme) in this aspect of the invention.

The method of admixing fibrinogen and thrombin may involve squirting or spraying the components simultaneously or sequentially to the repair site with a syringe or a related device. The mixing may result from two syringes held together along their barrels and at the plunders with two components mixed either after exiting the needles or in the hub just prior to exiting. Other devices may be used to produce an aerosol or to spray in a variable pattern, depending on the application.

Although various derivatives of fibrinogen have been used in clinical applications for some time, there are several safety issues involved in the clinical use of fibrinogen such as concern over viral contamination, especially with products containing fibrinogen or components prepared from human blood especially pooled human blood. Although improvements in viral cleansing techniques for blood products have been made since the fear of transmission of pathogenic viruses was brought to the surface, so that the risk of disease transmission has been greatly reduced, the risk has not been totally eliminated. The present invention, which relates to fibrinogen obtained from milk or urine, can be substantially free from such a concerns.

A twelfth aspect of the invention provides fibrinogen, according to the fourth to eighth aspects of the invention, for use in medicine. Preferably the fibrinogen is used in human medicine, However, it may also be used in veterinary medicine such as for horses, pigs, sheep, cows, cattle, rabbits, mice and rats as well as for domestic pets such as dogs and cats.

While the main use of fibrinogen is thought to be for the preparation of adhesive or sealing agents as hereinbefore described, fibrinogen has other applications in the field of medicine, for example as a coating for polymeric articles as disclosed in U.S. Pat. No. 5,272,074. A particular use of lyophilised fibrinogen of the present invention is within or part of a gauze or bandage (preferably made from polylactic acid compounds used in surgical stitches). Such a wound dressing can be supplied (also incorporating the other components required for the formation of a clot (described above), optionally in a package or kit form, for application direct to the skin or to an internal organ. All details and features of previously discussed aspects, also apply to the twelfth.

A thirteenth aspect of the invention provides a fibrin adhesive or sealant, according to the ninth aspect of the invention, for use in medicine.

The use in medicine may be any of those described herein. All details and features of aspects one to eleven, also apply to the thirteenth.

A fourteenth aspect of the present invention provides a method of surgery or therapy comprising placing fibrinogen according to the fourth to eighth aspects of the invention, on or within a animal or a body part of an animal. The animal in question is preferably in need thereof. Preferably the animal is a human. The fibrinogen may be mixed with one or more of thrombin, Factor XIII, Factor XIIIa or $Ca^{2+}$ separately, sequentially or simultaneously with the fibrinogen. The fibrinogen may thus be in the form of a sealant according to the ninth aspect of the invention. The fibrinogen may be applied by squirting using a syringe or a related device. It may be applied very precisely in a localised area or broadly over a wide area to any tissue. All details and preferred features of aspects one to thirteenth also apply to the fourteenth.

A fifteenth aspect of the invention provides the use of fibrinogen, according to the fourth to eighth aspects of the invention in the manufacture of a fibrin adhesive or sealant.

In this invention, purification of fibrinogen is achieved or a preferred optional step by the use of Hydrophobic Interaction Chromatography (HIC) which is carried out in such a way that enables not only the separation of milk proteins, leading to a substantially pure product, but also the simultaneous fractionation of fibrinogen into F1, F2 and degradation products. In general, fibrinogen, preferably partially purified by precipitation, is contacted with a HIC resin (e.g. Butyl SEPHAROSE (cross-linked beaded agarose) under conditions where the fibrinogen is retained (e.g. 0.2–0.8M, preferably 0.3 to 0.6M, ammonium sulphate). The resin is then washed, either in batch fashion by centrifugation or by inclusion in a chromatography column. Elution of bound material is facilitated by decreasing the concentration of salt (e.g. ammonium sulphate in decreasing concentration 0.5 to 0M) in the mobile phase so that resolution of fibrinogen from non-fibrinogen components is achieved. By careful selection of salt concentration, the fibrinogen is not only separated from the majority of milk components but can also be fractionated into subfamilies. Elution can either be carried out using a decreasing gradient whereby the slope of the gradient determines the resolution or, more conveniently, by use of a series of decreasing steps of concentration. The use of HIC enables the fibrinogen product to be defined with respect to its Aα C-terminal region The plasminogen activation system in milk has been a focus of interest for a number of years. It is generally accepted that milk contains the primary enzymes responsible for fibrinolysis in vivo e.g. plasminogen activator (both tissue type, tPA and urokinase type, uPA), plasminogen and plasmin. The action of proteolysis is often observed during storage of milk or milk products where casein appears to be the milk protein most susceptible to degradation. It was soon illustrated that in milk, plasminogen activators, plasminogen and plasmin were associated mainly with the casein micelles and not in the whey (or serum) phase. The mechanism by which these molecules associate with casein has not been categorically determined but it is probable that as these molecules contain Kringle domians (structured polypeptide chains with an affinity for basic amino acids) these domains probably mediate their interaction with casein.

It is realized that proteolysis of the human protein may occur within the mammary gland or udder of the lactating transgenic animal. The incubation period of the transgenic protein in the mammary gland or udder can be approximated to the time period between milking of the animal. Therefore it is apparent that increasing the frequency of milking minimizes this time period. However, increasing the frequency of milking to above 3 or 4 milkings per day not only creates a measure of discontinuity for the animal but involves a cost addition to Dairy expenses. It is accepted therefore that a measure of degradation of the human fibrinogen will occur. As discussed in the Prior Art, the presence of fibrinogen degradation products in a fibrin tissue adhesive compromises the usefulness of the product and therefore any degradation products must be removed. This invention discloses how the inventors have discovered an extremely efficient way of achieving this which also allows the ratio of F1 and F2 fibrinogen in the final product to be selected and defined.

Techniques for the separation of plasma fibrinogen into its various sub-fractions, as described in the prior art, generally fall into two categories. Those which rely on the differential solubility of subfractions in high concentration of salts (e.g. ammonium sulphate and glycine), often refereed to as selective precipitation techniques [Holm et al., Purification and Characterisation of 3 Fibrinogens with different molecular weights obtained from normal human plasma, Thrombosis Research, 37:165–176, 1985], and those which take advantage of the fact that degradation products have a different molecular size and can therefore be separated using size exclusion chromatography.

The two categories of techniques described above are quite contrasting in their ability and ease of use, at industrially enabling scales, for subfractionating fibrinogen. While precipitation techniques are relatively easy to operate and scale, their inherent mode of separation does not allow for the extremely high levels of resolution that would be required to ensure that the fibrinogen produced could be accurately defined with respect to its F1:F2 ratio and hence Aα. chain integrity. Indeed, advocates of this technique at the laboratory scale often report contamination of subfractions with each other [Lipinska et al., Fibrinogen Heterogeneity in Human Plasma: Electrophoretic demonstration and characterization of two major fibrinogen components, Journal of Laboratory & Clinical Chemistry, 84:509–516, 1974] and low yields.

In contrast to techniques based on differential solubility, size exclusion chromatography can potentially result in very good resolution of fibrinogen sub-fractions in high yield. The main drawbacks of this technique are expense and scale. Although F1 & F2 fibrinogen and F2 & F3 differ by some 35–40 Kdal, the size of the molecule itself (340 Kdal) is near the limit of the fractionation range of most size exclusion matrices. This results in poor resolution if expensive resins are not used. Another limitation is scale, as SEC is not a chromatographic technique favored at process scale when subtle separations have to be carried out. Also, SEC is usually a very expensive technique as only a small fraction of a column volume of material could be loaded while maintaining resolution.

Hydrophobic Interaction Chromatography (HIC) is a separations technique which exploits the binding of proteins to mildly hydrophobic resins in the presence of low concentrations of salts which expose hydrophobic patches on the surface of proteins. In the presence of these so-called "structure forming" salts, selective interactions can be initiated between different proteins and the matrix. The technique is most often used to discriminate between different proteins in a heterogeneous mixture. The inventors have discovered that not only is HIC a very good fractionation technique for the recovery of fibrinogen from a partially purified extract, it is also a surprisingly powerful technique for resolving fibrinogen subfractions i.e. F1, F2, F3 (Fragment X), Fragment Y and Fragments D & E.

Transgenic human fibrinogen partially purified from milk is bound to HIC resins (e.g. but not exclusively Butyl SEPHAROSE (cross-linked beaded agarose) 4FF. Amersham Pharmacia Biotechnology) in the presence of ammonium sulphate or other "structure forming" salt at a concentration enabling fibrinogen to bind e.g. a range 0.2–1.0M (preferably 0.3–0.6M) is used. By decreasing the concentration of ammonium sulphate in the irrigation buffer. the bound material elutes from the column in the order milk components (0.485–0.37M ammonium sulphate), F1 fibrinogen (0.37–0.2M ammonium sulphate), F2 fibrinogen (0.2–0.14M ammonium sulphate) and F3 fibrinogen and degradation products (0.10–0.0M ammonium sulphate). The range of concentrations of ammonium sulphate over which the bound components elute is determined, in part, by the operating conditions and those skilled in the art would be able to adjust either the temperature or the pH or both to change the concentrations of ammonium sulphate over which the fractions elute. Using this technique it is possible by means of gradient elution or more preferably by a series of steps to predetermine and thus define the fibrinogen that it is eluted from the column in terms of its F 1 to F2 ratio and hence its Aα chain integrity.

This text refers to the accompanying figures of which:

FIGS. 6, 7, 8 and 9 are RP-HPLC chromatograms for fibrinogen and fibrinogen fractions eluted from the HIC column using, conditions outlined in examples 1 and 2. The chromatograms were generated using a wavelength of 214 nm.

The following non limiting examples help to illustrate this invention.

EXAMPLE A

Milk from a transgenic ewe was thawed from a frozen state in a water bath at 37° C. and then delipidated by low speed centrifugation (2000 rpm) for 10 minutes. The skimmed milk was than aliquoted into 2×40 ml fractions and processed as follows. To one of the fractions was added 40 ml of 27.6% (w/v) ammonium sulphate in 25 mM citrate, 100 mM εACA, pH 8.0. The tube was mixed for 20 minutes at room temperature followed by high speed centifugation in a Beckman J2–21 centrifuge (15° C.). The supernatant generated was removed and the pellet dissolved in 25 mM citrate, pH 8.0. Once dissolved up to 40 ml, the precipitation and resolubilisation was repeated as above. A final precipitation and resolubilisation step was then carried out, essentially as above except that εACA was omitted from the salt solution. The same process as above was then repeated on the second 40 ml aliquot of skimmed milk except that εACA was not used.

Figure 1:
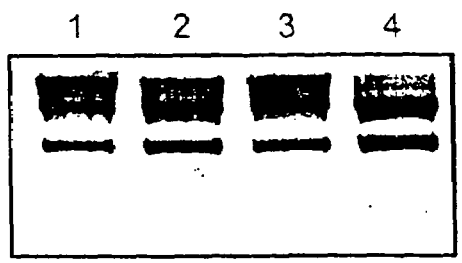
FIG. 1 is SDS-PAGE of part purified fibrinogen from example A. in the absence or presence of εACA.

The Sodium Dodecyl Sulphate PolyAcrylamide Gel Electrophoresis (SDS-PAGE, 8–16%, Novex) shown as FIG. 1 illustrates the stability of part purified fibrinogen. Lane 1 represents fibrinogen part purified in the presence of εACA and stored at 4° C. overnight. It can be seen that the fibrinogen is predominantly F1:F2. The degradation product. Fragment X (F3) is also present as a faster migrating band under the F1:F2 bands. Lane 2 represents material stored at 4° C. purified as in Lane 1 except that εACA was absent during the precipitation stage. From Lane 1 and Lane 2, it is evident that some F1 fibrinogen has been proteolytically cleaved even during storage at 4° C. Lane 3 represents material as in lane 1 except that storage was at 18° C. Overnight. As can be seen this material appears to be more stable than that shown in Lane 2 and in fact is very similar to that shown in Lane 1. Lane 4 represents material purified in the absence of εACA after overnight storage at 18° C. It is evident that this material has been severely damaged and is almost lacking in F1 fibrinogen. This example serves to illustrate that fibrinogen, part purified from milk by precipitation, is unstable to milk protease action. This protease action may be diminished by incubation at 4° C. but is abolished if the precipitation is carried out in the presence of εACA which prevents milk protease contamination of the precipitated fibrinogen.

EXAMPLE 1

Figure 3:
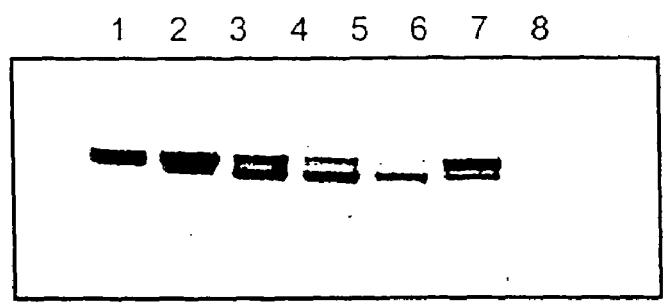
FIG. 3 is SDS-PAGE of transgenic human fibrinogen elution from an HIC (Butyl SEPHAROSE (cross-linked beaded agarose) 4FF) column in example 1.
Figure 2:
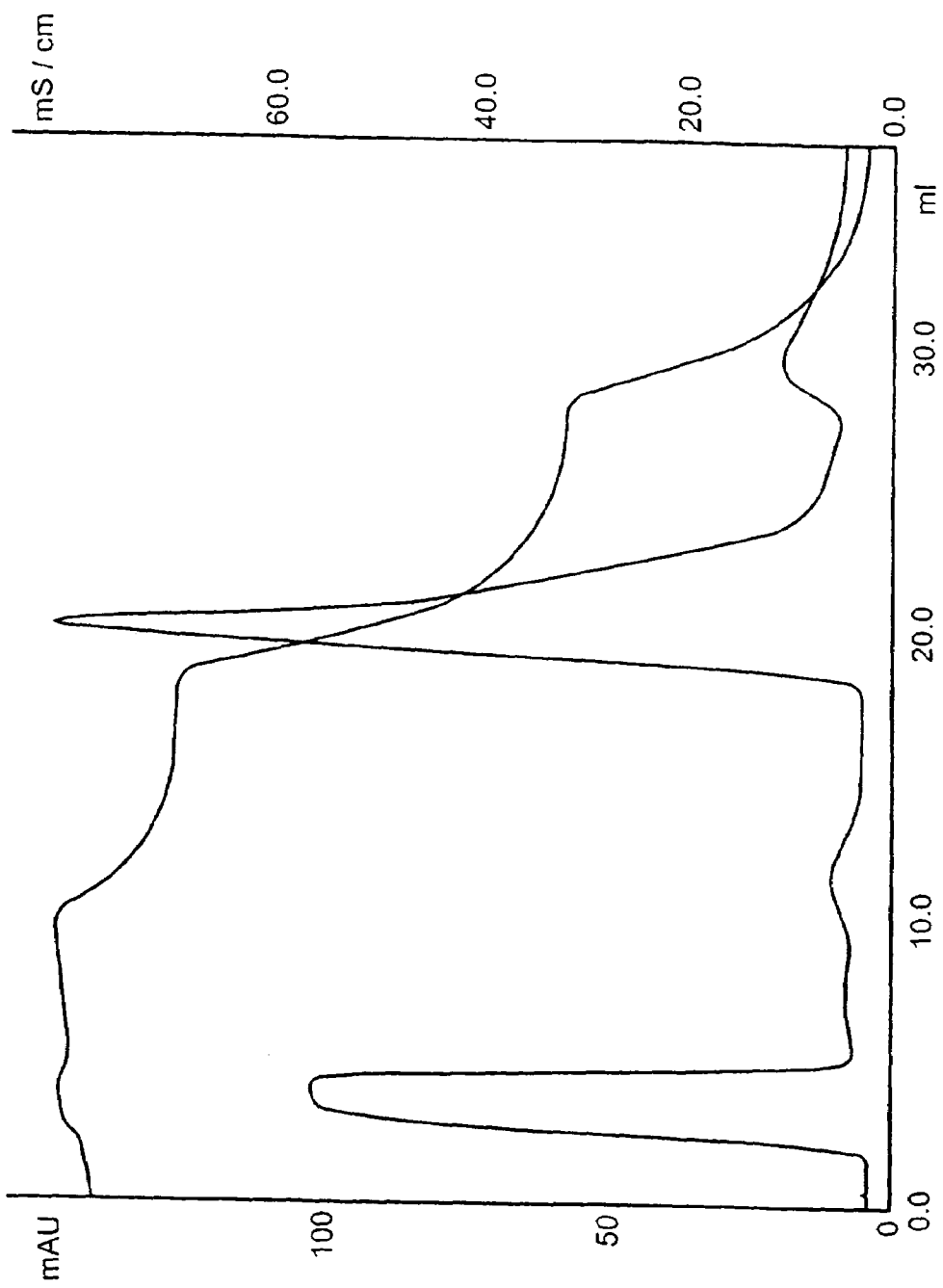
FIG. 2 is a chromatogram illustrating the various fractions generated from the HIC column in example 1. The chromatogram was generated using UV at 280 nm.

Transgenic fibrinogen was, partially purified from the milk of a transgenic ewe by precipitation with ammonium sulphate, in a similar manner as described in example A. 2 ml was made to 0.485M ammonium sulphate by the addition of 1.45M ammonium sulphate in 5 mM citrate, pH 7.5 (1 ml). After mixing, the solution was pumped onto a HiTrap Butyl SEPHAROSE (cross-linked beaded agarose) 4FF column (previously equilibrated with 0.485M ammonium sulphate, in 25 mM citrate buffer. pH 7.5) at 0.1 ml/min. The column was washed with 2 column volumes of 0.485M ammonium sulphate in 5 mM citrate, pH 7.5 after which elution was carried out in 3 steps 1) 0.40M ammonium sulphate in 5 mM citrate, pH 8.0, 2) 0.15M ammonium sulphate in 5 mM citrate buffer., pH 8.0, 3) 5 mM citrate pH 8.0. The chromatogram presented below as FIG. 2 shows that 4 major peaks were obtained from this experiment. The first peak represents material that does not bind to the column under these adsorption conditions and is mainly sheep milk proteins. The second peak represents material that did bind to the column and was eluted with 0.40M ammonium sulphate. The third peak represents fibrinogen and fractions taken across this are shown on a SDS-PAGE as FIG. 3. The clear distinction between F1 (High molecular weight fibrinogen) and F2 (Low molecular weight fibrinogen) and the resolution obtained on the chromatography can be clearly seen (Lanes 1–5). Lane 6 represents the pooled peak while lanes 7 & 8 represent peak 4 from the chromatogram which can be seen to be F3 (Fragment X) fibrinogen. Thus it is evident that by changing the concentration of ammonium sulphate used for elution it is possible to define eluted fibrinogen with respect to its Aα chain integrity

EXAMPLE 2

In another example which illustrates the scale-up potential of this technique, a procedure equivalent to example 1 above was scaled up by a factor of 400. Thus 0.9 g (790 ml) of transgenic human fibrinogen was partially purified by precipitation in the presence of 50 mM ε-aminocaproic acid. It was then made to 0.5M ammonium sulphate by the addition of 790 ml of 1M ammonium sulphate in 5 mM citrate buffer pH 7.5. This material was loaded onto a column 5 cm×21 cm (400 ml) of Butyl SEPHAROSE (cross-linked beaded agarose) 4FF at a flow rate of 20 ml/min. After loading, the column was washed with 400 ml of 0.5M ammonium sulphate in 5 mM citrate buffer, pH 7.5. Bound material was eluted from the column by irrigation with three buffers 1) 0.4M ammonium sulphate in 5 mM citrate, pH 7.5, 800 ml 2) 0.15M ammonium sulphate in 5 mM citrate buffer, pH 7.5. 800 ml, and 3) 5 mM citrate, pH 7.5, 800 ml.

Figure 4:
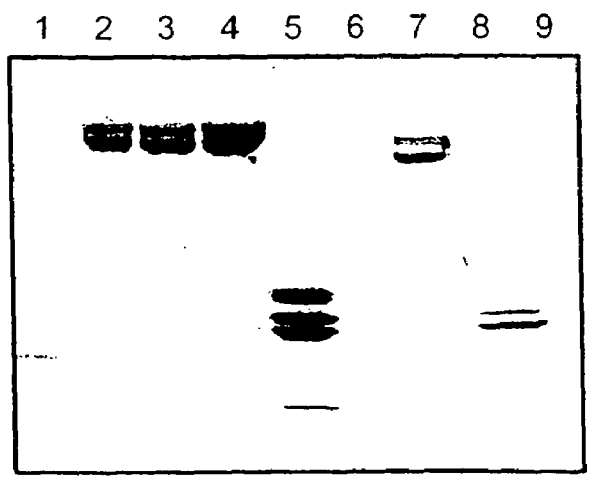
FIG. 4 is SDS-PAGE of transgenic human fibrinogen elution from an HIC (Butyl SEPHAROSE (Coss-linked beaded agarose) 4FF) column in example 2.
Figure 5:
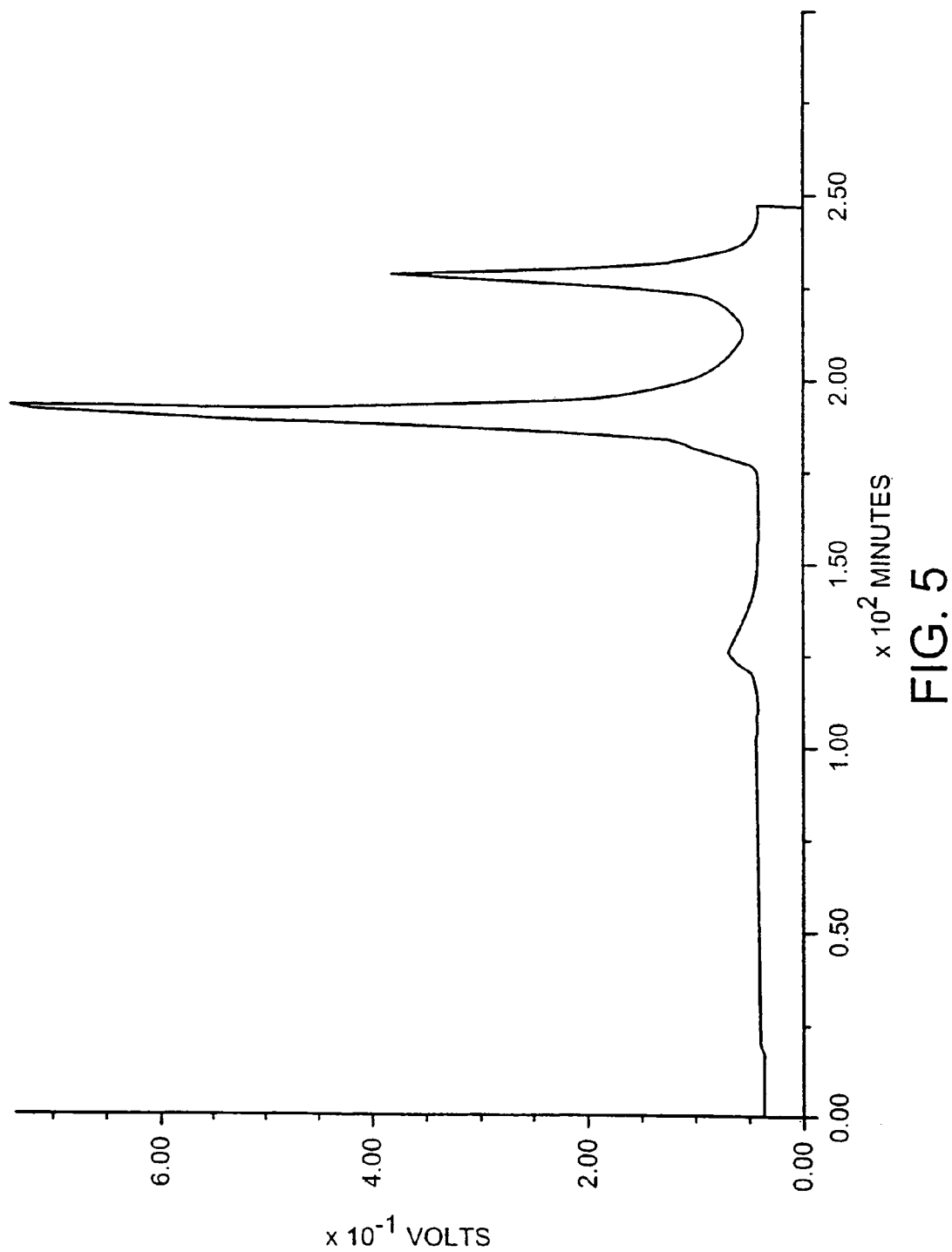
FIG. 5 is chromatogram illustrating the various fractions generated from the HIC column in example 2. The chromatogram was generated using UV.

The SDS-PAGE and chromatogram shown as FIGS. 4 and 5 respectively, show results for this experiment. As can be seen from the SDS-PAGE, F1:F2 fibrinogen was eluted from the column by 0.15M ammonium sulphate (Lanes 3–4. FIG. 4) while F3 fibrinogen was eluted using a step change to 5 mM citrate, pH 7.5 containing no ammonium sulphate (Lane 8, FIG. 4). Reducing SDS-PAGE is a convenient way of determining Aα chain integrity as loss of Aα C-terminal regions results in a decrease in the Aα chain molecular weight. This decrease is readily qualitatively assessed. In FIG. 4, Lane 6 shows a reduced F1:F2 fibrinogen with 10 mM dithiotheritol as the reducing agent. When this is compared to F3 fibrinogen (Lane 8), the loss of Aα chain is clearly seen.

Figure 6:
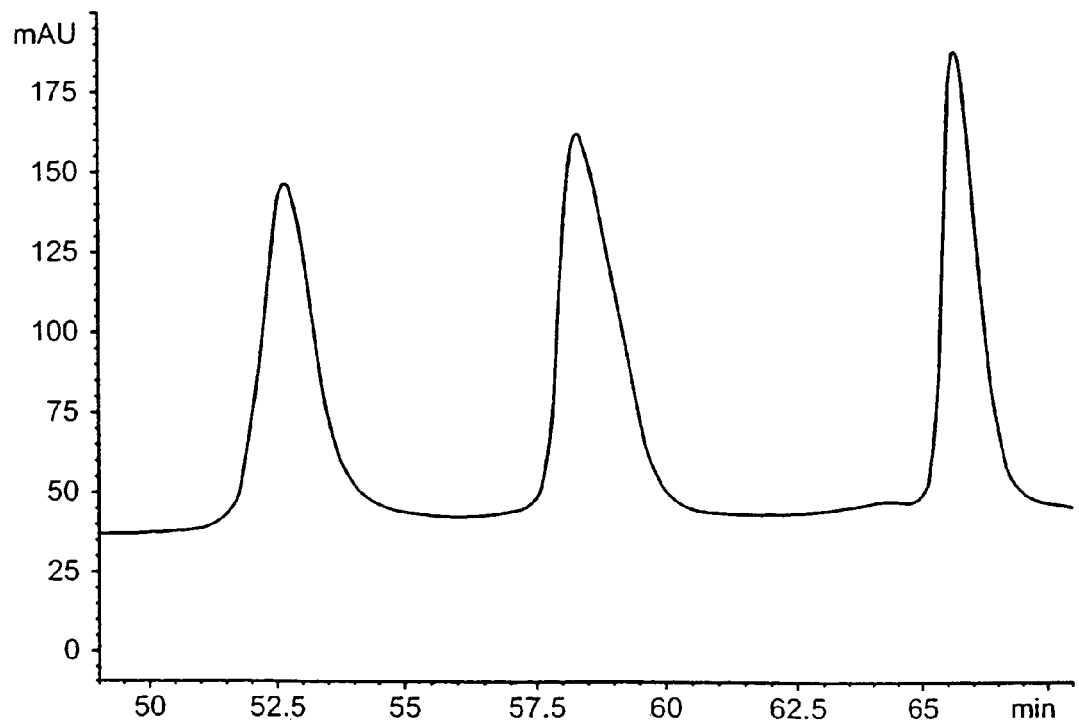
Figure 7:
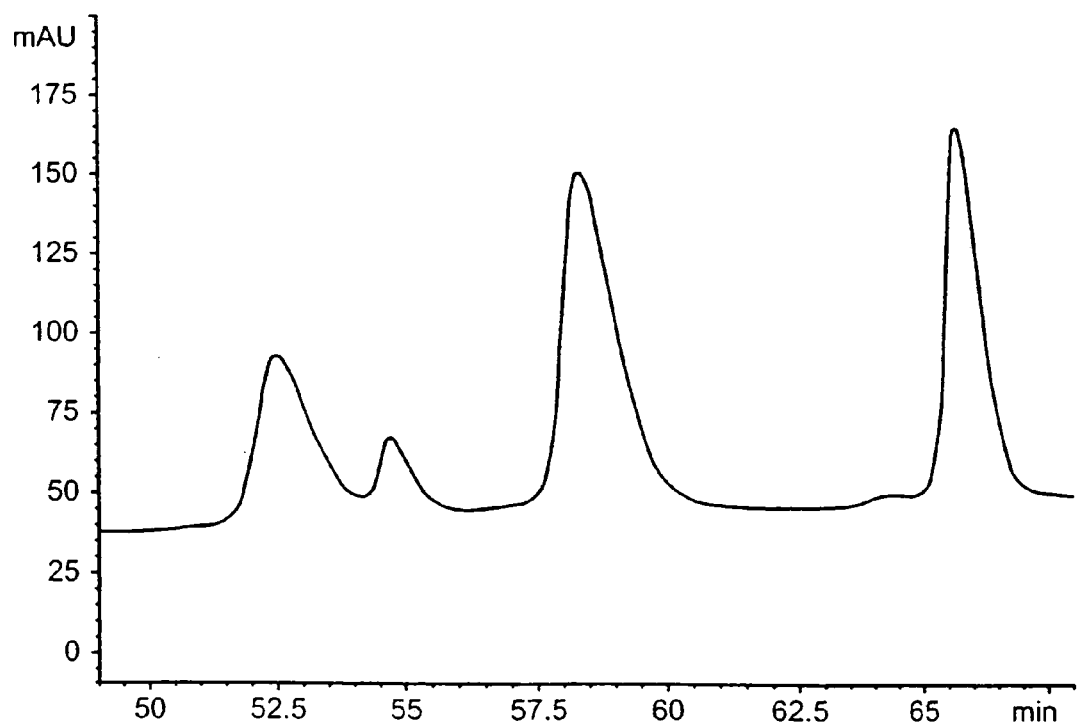
Figure 8:
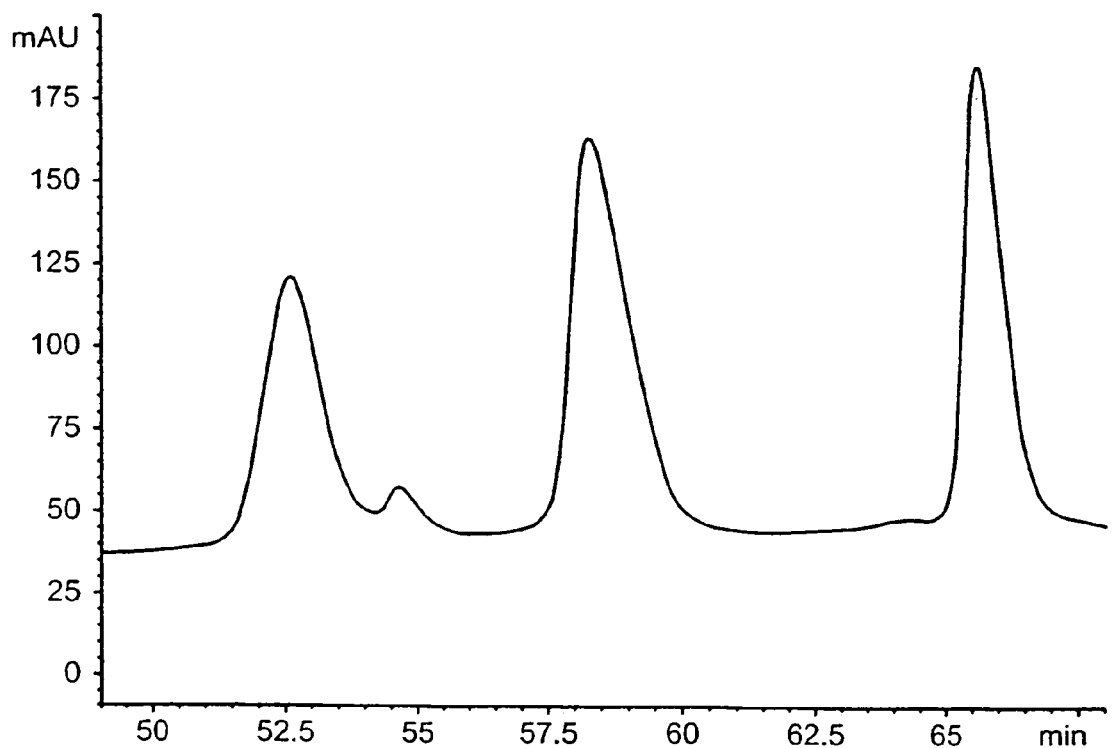
Figure 9:
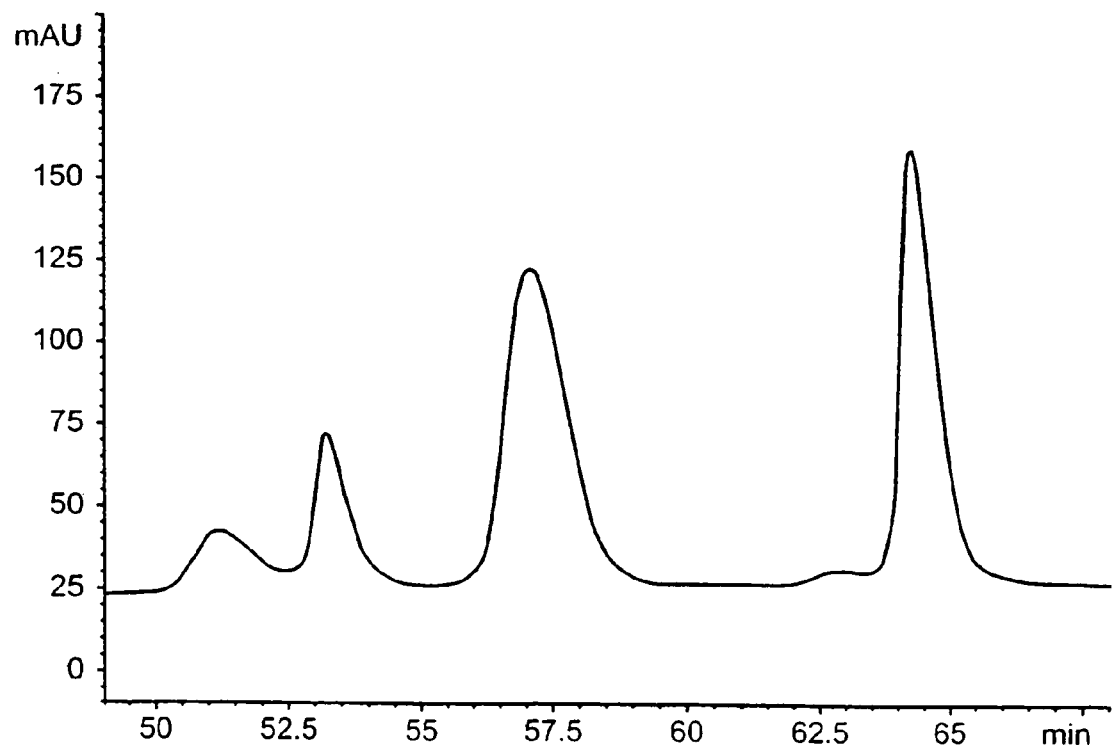

Quantitative information on Aα chain integrity can be obtained by the use of Reversed-Phase High Performance Liquid Chromatography (RP-HPLC) on reduced fibrinogen according to Raut et al., [Ultra-rapid preparation of milligram quantities of the purified polypeptide chains of human fibrinogen, Journal of Chromatography B, 660:390–394, 1994] which allows for integration of peak areas. FIG. 6 shows a RP-HPLC chromatogram for purified F1 fibrinogen; the three fibrinogen chains elute from the column in the order Aα, Bβ and γ respectively; as can be seen, there exists a single peak for each chain. Integration of the Aα chain results in a peak area which is used as a standard against which fibrinogen with degraded Aα chains can be normalized. In FIG. 7, a RP-HPLC chromatogram, run under identical conditions to that in FIG. 6, is shown for F2 fibrinogen where it is evident that the Aα peak has been separated into two peaks, the former being intact Aα chain and the latter being Aα chain being proteolytically cleaved at the C-terminus. Using on-line integration it can be calculated that the Aα chain exist as 73% intact, the remaining 27% being degraded Aα chain. In FIG. 8 a RP-HPLC chromatogram is shown for F3 fibrinogen. In this chromatogram it is evident that amount of degraded Aα greatly outweighs the amount of non-degraded Aα chain as is illustrated by the much reduced non-degraded Aα chain peak. It can be calculated that degraded Aα chain represent 62% of total Aα chain present.

It is evident therefore that using the technique of RP-HPLC, as an analytical toot following Hydrophobic Interaction Chromatography, allows conditions for the Hydrophobic Interaction Chromatography to be selected to prepare fibrinogen with a defined Aα chain integrity. An example of this is Liven in FIG. 9 which represents elution from the Butyl SEPHAROSE (Cross-linked beaded agarose) 4 FF column using conditions outlined in Example 2 above. From the chromatogram in FIG. 9 it is evident that mainly F1 fibrinogen is selected as the Aα chain is 87% intact.

The invention claimed is:

1. A method for part purification of fibrinogen having a high Aα-chain integrity from milk, comprising the following steps:
   a) precipitating the fibrinogen from milk;
   b) separating the precipitated fibrinogen from protease enzymes contained in whey and thereby recovering a part-purified fibrinogen, wherein said part-purified fibrinogen comprises high and low molecular weight sub-fractions;
   c) contacting the part-purified fibrinogen with a hydrophobic interaction chromatography resin under conditions wherein the fibrinogen binds to the resin; and
   d) removing the bound fibrinogen by means of elution, wherein elution results in the selective removal of said fibrinogen sub-fractions to produce high Aα-chain integrity fibrinogen.

2. The method of claim 1, wherein the precipitation step, separation step, or both are achieved in the presence of lysine, a lysine analogue, ε-aminocaproic acid, or a combination thereof.

3. A method for obtaining fibrinogen having a high Aα-chain integrity from milk derived from a transgenic mammal, the method comprising:
   (a) contacting the milk with a hydrophobic interaction chromatography resin under conditions wherein the fibrinogen in the milk binds to the resin, wherein said fibrinogen comprises high and low molecular weight sub-fractions; and
   (b) removing the bound fibrinogen by means of elution, wherein elution results in the selective removal of said fibrinogen sub-fractions to produce high Aα-chain integrity fibrinogen.

4. The method of claim 1, wherein the protease enzyme is plasmin, plasminogen, or combination thereof.

5. The method of claim 1, wherein the milk comprises whole milk, skimmed milk, or a milk fraction.

6. The method of claim 1, wherein the milk is derived from a sheep, cow, goat, rabbit, camel, water buffalo, pig or horse.

7. The method of claim 1, wherein the fibrinogen is bovine or human derived.

* * * * *